(12) United States Patent
Ashby et al.

(10) Patent No.: US 7,335,219 B1
(45) Date of Patent: Feb. 26, 2008

(54) HEMOSTATIC DEVICE INCLUDING A CAPSULE

(75) Inventors: Mark Ashby, Laugna Niguel, CA (US); Tin Trong Tran, Anaheim, CA (US)

(73) Assignee: Sub-Q, Inc., San Clemente, CA (US)

( * ) Notice: Subject to any disclaimer, the term of this patent is extended or adjusted under 35 U.S.C. 154(b) by 18 days.

(21) Appl. No.: 10/460,859

(22) Filed: Jun. 12, 2003

Related U.S. Application Data

(63) Continuation-in-part of application No. 10/287,922, filed on Nov. 4, 2002.

(51) Int. Cl.
*A61B 17/08* (2006.01)
*A61D 1/00* (2006.01)

(52) U.S. Cl. ..................... 606/213; 128/887

(58) Field of Classification Search .......... 606/213, 606/214; 128/887
See application file for complete search history.

(56) References Cited

U.S. PATENT DOCUMENTS

| 581,235 A | 4/1897 | Kenyon |
| 1,578,517 A | 3/1926 | Hein |
| 2,086,580 A | 7/1937 | Shirley |
| 2,465,357 A | 3/1949 | Correll |
| 2,492,458 A | 12/1949 | Bering, Jr. |
| 2,507,244 A | 5/1950 | Correll |
| 2,558,395 A | 6/1951 | Studer |
| 2,597,011 A | 5/1952 | MacMasters et al. |
| 2,680,442 A | 6/1954 | Linzmayer |
| 2,761,446 A | 9/1956 | Reed |
| 2,814,294 A | 11/1957 | Figge |
| 2,824,092 A | 2/1958 | Thompson |
| 2,899,362 A | 8/1959 | Sieger, Jr. et al. |
| 3,157,524 A | 11/1964 | Artandi |
| 3,724,465 A | 4/1973 | Duchane |
| 4,000,741 A | 1/1977 | Binard et al. |
| 4,077,409 A | 3/1978 | Murray et al. |
| 4,211,323 A | 7/1980 | Olsen |

(Continued)

FOREIGN PATENT DOCUMENTS

EP 0032826 7/1981

(Continued)

OTHER PUBLICATIONS

Allison, D., et al., "Percutaneous liver biopsy and track embolization with steel coils", Radiology, vol. 169, pp. 261-263, (1998).

(Continued)

*Primary Examiner*—Michael J. Hayes
*Assistant Examiner*—Michael Mendoza
(74) *Attorney, Agent, or Firm*—Miller Matthias Hull

(57) ABSTRACT

An apparatus for inhibiting blood loss from a puncture site. The apparatus may include means for locating a puncture site in a blood vessel wall. This apparatus is comprised of a tube and an elongated member that is positioned around the tube. The elongated member includes a proximal end and a distal end. Around the tube is also a dissolvable distal capsule, the distal capsule including a proximal end and a distal end, wherein the proximal end of the distal capsule attaches to the distal end of the elongated member. Inside the distal capsule is hemostatic material such as a sponge.

24 Claims, 13 Drawing Sheets

U.S. PATENT DOCUMENTS

| | | |
|---|---|---|
| 4,218,155 A | 8/1980 | Weidner |
| 4,238,480 A | 12/1980 | Sawyer |
| 4,292,972 A | 10/1981 | Pawelchak |
| 4,323,072 A | 4/1982 | Rosenbluth et al. |
| 4,340,066 A | 7/1982 | Shah |
| 4,390,018 A | 6/1983 | Zuloowski |
| 4,404,970 A | 9/1983 | Sawyer |
| 4,515,637 A | 5/1985 | Cioca |
| 4,573,576 A | 3/1986 | Krol |
| 4,587,969 A | 5/1986 | Gillis |
| 4,588,395 A | 5/1986 | Lemelson |
| 4,619,261 A | 10/1986 | Guerriero |
| 4,619,913 A | 10/1986 | Luck et al. |
| 4,645,488 A | 2/1987 | Matukas |
| 4,708,718 A | 11/1987 | Daniels |
| 4,744,364 A | 5/1988 | Kensey |
| 4,790,819 A | 12/1988 | Li et al. |
| 4,829,994 A | 5/1989 | Kurth |
| 4,850,960 A | 7/1989 | Grayzel |
| 4,852,568 A | 8/1989 | Kensey |
| 4,890,612 A | 1/1990 | Kensey |
| 4,900,303 A | 2/1990 | Lemelson |
| 4,929,246 A | 5/1990 | Sinofaky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,053,046 A | 10/1991 | Janese |
| 5,061,274 A | 10/1991 | Kensey |
| 5,080,655 A | 1/1992 | Haaga |
| 5,108,421 A | 4/1992 | Fowler |
| 5,163,904 A | 11/1992 | Lampropoulos et al. |
| 5,167,624 A | 12/1992 | Butler et al. |
| 5,192,300 A | 3/1993 | Fowler |
| 5,192,301 A | 3/1993 | Kamiya et al. |
| 5,195,988 A | 3/1993 | Haaga |
| 5,220,926 A | 6/1993 | Jones |
| 5,221,259 A | 6/1993 | Weldon et al. |
| 5,242,683 A | 9/1993 | Klaveness |
| 5,254,105 A * | 10/1993 | Haaga ..................... 604/265 |
| 5,275,616 A | 1/1994 | Fowler |
| 5,282,827 A | 2/1994 | Kensey et al. |
| 5,299,581 A * | 4/1994 | Donnell et al. ............. 128/830 |
| 5,310,407 A | 5/1994 | Casale |
| 5,322,515 A | 6/1994 | Karas et al. |
| 5,324,306 A | 6/1994 | Makower et al. |
| 5,325,857 A | 7/1994 | Nabai et al. |
| 5,334,216 A | 8/1994 | Vidal et al. |
| 5,366,480 A | 11/1994 | Corriveau et al. |
| 5,370,656 A | 12/1994 | Shevel |
| 5,383,896 A | 1/1995 | Gershony et al. |
| 5,383,899 A | 1/1995 | Hammersiag |
| 5,385,550 A | 1/1995 | Su et al. |
| 5,388,588 A | 2/1995 | Nabai et al. |
| 5,391,183 A | 2/1995 | Janzen et al. |
| 5,399,361 A | 3/1995 | Song et al. |
| 5,417,699 A | 5/1995 | Klein |
| 5,419,765 A | 5/1995 | Weldon et al. |
| 5,431,639 A | 7/1995 | Shaw |
| 5,437,292 A | 8/1995 | Kipshidze |
| 5,437,631 A | 8/1995 | Janzen |
| 5,443,481 A | 8/1995 | Lee |
| 5,467,780 A | 11/1995 | Nabai et al. |
| 5,478,352 A | 12/1995 | Fowler |
| 5,479,936 A | 1/1996 | Nabai et al. |
| 5,486,195 A | 1/1996 | Myers |
| 5,490,736 A | 2/1996 | Haber |
| 5,522,840 A | 6/1996 | Krajicek |
| 5,522,850 A | 6/1996 | Yomtov et al. |
| 5,526,822 A | 6/1996 | Burbank et al. |
| 5,527,332 A | 6/1996 | Clement |
| 5,529,577 A | 6/1996 | Hammershiag |
| 5,540,715 A | 7/1996 | Katsaros et al. |
| 5,542,914 A | 8/1996 | Van Iten |
| 5,545,178 A | 8/1996 | Kensey et al. |
| 5,554,108 A * | 9/1996 | Browning et al. ............ 604/15 |
| 5,558,853 A | 9/1996 | Quay |
| 5,591,204 A | 1/1997 | Janzen et al. |
| 5,591,205 A | 1/1997 | Fowler |
| 5,601,602 A | 2/1997 | Fowler |
| 5,601,603 A | 2/1997 | Illi |
| 5,645,566 A | 7/1997 | Brenneman et al. |
| 5,645,849 A * | 7/1997 | Pruss et al. ................. 424/426 |
| 5,649,547 A | 7/1997 | Ritchart et al. |
| 5,653,730 A | 8/1997 | Hammersiag |
| 5,665,107 A | 9/1997 | Hammersiag |
| 5,676,689 A | 10/1997 | Kensey |
| 5,681,279 A | 10/1997 | Roper et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,769,813 A | 6/1998 | Peiler et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,830,130 A | 11/1998 | Janzen et al. |
| 5,858,008 A | 1/1999 | Capaccio |
| 5,868,762 A | 2/1999 | Cragg et al. |
| 5,902,310 A | 5/1999 | Foerster et al. |
| 5,984,950 A | 11/1999 | Cragg et al. |
| 6,007,563 A | 12/1999 | Nash et al. |
| 6,027,471 A | 2/2000 | Fallon et al. |
| 6,027,482 A | 2/2000 | Imbert |
| 6,071,300 A | 6/2000 | Brenneman et al. |
| 6,071,301 A | 6/2000 | Cragg et al. |
| 6,086,607 A | 7/2000 | Cragg et al. |
| 6,161,034 A | 12/2000 | Burbank et al. |
| 6,162,192 A | 12/2000 | Cragg et al. |
| 6,183,497 B1 | 2/2001 | Sing et al. |
| 6,197,327 B1 * | 3/2001 | Harrison et al. ............ 424/430 |
| 6,200,328 B1 | 3/2001 | Cragg et al. |
| 6,315,753 B1 | 11/2001 | Cragg et al. |
| 6,610,025 B2 | 8/2003 | Berg et al. |
| 6,984,219 B2 | 1/2006 | Ashby et al. |

FOREIGN PATENT DOCUMENTS

| | | |
|---|---|---|
| EP | 0476178 | 3/1992 |
| EP | 0482350 | 4/1992 |
| EP | 0557963 | 2/1993 |
| EP | 0637431 | 11/1994 |
| FR | 2641692 | 7/1990 |
| GB | 1509023 | 4/1978 |
| GB | 1569660 | 6/1980 |
| SU | 782814 | 11/1980 |
| SU | 1088709 A | 4/1984 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 96/08208 | 3/1996 |
| WO | WO 96/24290 | 8/1996 |
| WO | WO 98/06346 | 2/1998 |
| WO | WO 99/66834 | 12/1999 |

OTHER PUBLICATIONS

J. Bryne Review Article: Endovascular treatments for intracranial anuerysms, 1996 The British journal of radiology; 98,891-899.

Chuang, V., et al., "Sheath needle for liver biopsy in high-risk patience", Radiology, vol. 166, pp. 261-262 (1988).

John T. Correll, et al., A new Physiologically absorbable sponge.
John T. Correll, et al. Biologic investigations of new absorbable sponge; p. 585.
Fandrich, C., et al. "Small guage gelfoam plug liver biopsy in high risk patients", Australian Radiology, vol. 40, pp. 230-234 (1996).
Foran, JPM, et al. "Early mobilisation after percutaneous cardiac catheterisation using collagen plug (vasoseal) maemostatis" BRHeart, vol. 69, pp. 424-429 (1993).
Gibbs, JSR, "Femoral arterial hemostasis" J. Interventional card, vol. 5, pp. 85-88 (1992).
Journal of interventional cardiology vol. 5 No. 2 June.
Kassell, et al. Size of Intracanial aneurysm; vol. 12, No. 3, (1983).
Kiemeneiji, F, et al., "Improved anticoagulation management after Palmaz Schatz coronary stent implantation by sealing the arterial puncture site with vascular hemostasis device", Catheterization and Cardiovascular diagnosis, vol. 30, pp. 1685-1692 (1995).
Kussmaul, WG, "Rapid arterial hemostasis", J. Am. Coll. Card., vol. 25, pp. 1685-1692 (1995).
Pharmacia & Upjohn manufacturer brochure gelfoam sterile sponge, sterile power and sterile film, pp. 1-34 (May 1997).
Pharmacia & Upjohn manufacturer brochure "gelfoam sterile powder", (Feb. 1996).
Pharmacia & Upjohn manufacturer brochure, "gelfoam sterile powder" (Mar. 1996).
Pharmacia & Upjohn manufacturer brochure (Sep. 1996).
Pharmacia & Upjohn manufacturer specification, "Gelfoam sterile sponge, sterile powder and sterile film" pp. 1-23 (Nov. 1996).
Riley, SA, Percutaneous liver biopsy with plugging of needle track: a safe method for use in patients with impaired coagulation, The lancet, p. 436 (1964).
Sanborn, T. Multicenter randomized trial comparing percutaneous collagen hemostasis device with conventional manual compression after diagnostic angiography and angioplasty , J. Am. Coll. Card., vol. 22, pp. 1273-1279, (1993).
Schievink, et al. The new england journal of medicaine; review articles; intracanial aneurysms; Jan. 2, 1997.
Scharader, R. "Collagen appl.", Catheterization & cardiovascular diagnosis (1992) pp. 298-302.
Silber, S., "Rapid hemostasis of arterial puncture sites with collagen in patients undergoing diagnostic interventional cardiac catherterization", clinical cardiology, vol. 20, pp. 981-992, (1997).
Smith, T., "Percutaneous transhepatic liver biopsy with tract embolization", Radiology, vol. 198, pp. 769-774 (1996).
Szikora, et al. Combined Use of stents and cells to treat experimental wide-necked carotid aneuryms: Preliminary results; AJNR AM newradiol 15: 1091-1102, Jun. 1994.
Szikora, et al. Endovascular treatment of experimental anuerysms with liquid polymers: vol. 38, No. 2, Feb. 1996.
Turjman, et al. Combined stent implantation & endoascular coil placement for tretment of experimental wide-necked aneurysms:AJNRAM J. Neuroradio 15: 1087-1090 Jun. 1994.
Yoshimoto, et al cerebral anuerysms unrelated to arterial bifurcations; Acta neurochir (Wien) (96) 138: 958-964.
Zins, M., "US-guided percutaneous liver biopsy with plugging of the needle track" radiology, vol. 187, pp. 841-843, (1992).

* cited by examiner

FIG. 5
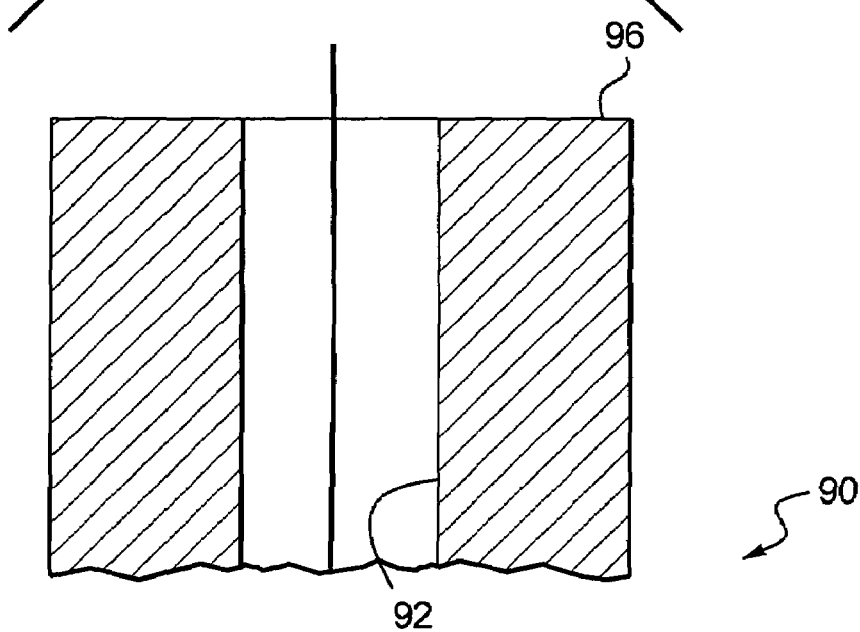
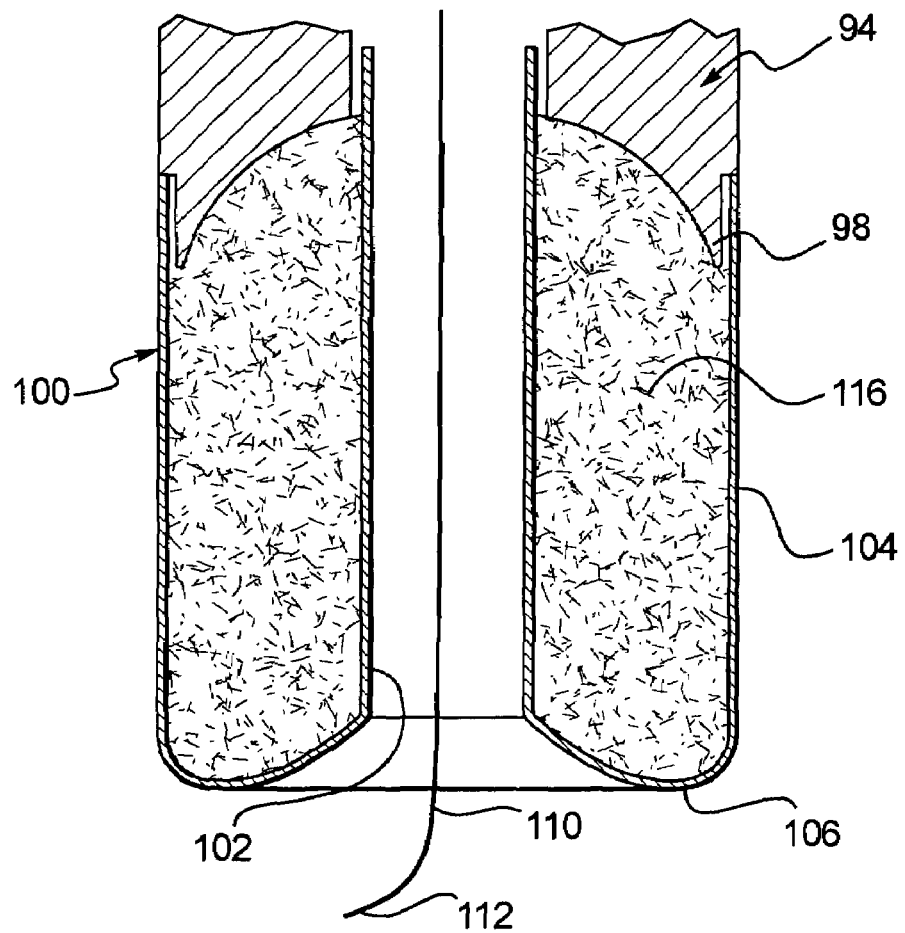

HEMOSTATIC DEVICE INCLUDING A CAPSULE

RELATED APPLICATION

This application is a Continuation in Part of prior co-pending U.S. patent application Ser. No. 10/287,922, titled "Apparatus and Method for Inhibiting Blood Loss", filed Nov. 4, 2002.

BACKGROUND OF THE INVENTION

1. Field of the Invention

The invention relates to hemostasis systems and methods for blood vessel puncture sites, biopsy tracts and other puncture wound sites.

2. Brief Description of the Related Art

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface and may be unsuitable for patients with substantial amounts of subcutaneous adipose tissue since the skin surface may be a considerable distance from the vascular puncture site.

Another approach to subcutaneous blood vessel puncture closure involves the delivery of non-absorbable tissue adhesives, such cyanoacrylate, to the perforation site. Such a system is disclosed in U.S. Pat. No. 5,383,899.

The application of an absorbable material such as collagen or a non-absorbable tissue adhesive at the puncture site has several drawbacks including: 1) possible injection of the material into the blood vessel causing thrombosis; and, 2) the inability to accurately place the absorbable material plug directly over the puncture site.

The use of an anchor and plug system addresses these problems to some extent but provides other problems including: 1) complex and difficult application; 2) partial occlusion of the blood vessel by the anchor when placed properly; and 3) complete blockage of the blood vessel or a branch of the blood vessel by the anchor if placed improperly. Another problem with the anchor and plug system involves reaccess. Reaccess of a particular blood vessel site sealed with an anchor and plug system is not possible until the anchor has been completely absorbed because the anchor could be dislodged into the blood stream by an attempt to reaccess.

Accordingly, it would be desirable to provide a system capable of accurately locating the blood vessel wall and delivering a hemostasis material over a puncture site. Likewise, following percutaneous needle biopsy of solid organs it is necessary to provide hemostasis.

Percutaneous needle biopsy of solid organs is one of the most common interventional medical procedures. Millions of percutaneous needle biopsies are performed annually in the United States and throughout the world. Percutaneous biopsy is a safe procedure which has supplanted surgical biopsy for many indications, such as kidney biopsy and liver biopsy.

Possible complications of needle biopsy include bleeding at the biopsy site. The amount of bleeding is related to a number of factors including needle size, tissue sample size, patient's coagulation status, and the location of the biopsy site. Vascular organs such as the liver, a common biopsy target, may bleed significantly after needle biopsy.

Sterile sponges, such as GELFOAM, are prepared in dry sterile sheets which are used as packing material during surgery for control of bleeding. The sponge sheets are left in the surgical site after surgery to stop bleeding and are absorbed by the body. A number of techniques have used these absorbable sterile sponge materials to plug a biopsy tract to minimize or prevent bleeding. The absorbable sponge provides a mechanical blockage of the tract, encourages clotting, and minimizes bleeding though the biopsy tract.

Accordingly, it would be desirable to provide a reliable technique for providing hemostasis at biopsy sites or other puncture wound sites.

SUMMARY OF THE INVENTION

According to one aspect of the present invention, a hemostasis device is provided including a hemostatic material such as gelatin sponge which is contained in a gelatin capsule. The hemostatic material and capsule device is delivered to a selected site in a mammalian body to provide hemostasis following interventional procedures such as percutaneous introduction of instrumentation into a vein or artery or percutaneous biopsy procedure. After delivery the capsule contacts blood or other fluids and dissolves, thereby releasing the hemostatic material which absorbs fluid and expands to provide hemostasis.

According to another aspect of the present invention improved capsules are disclosed for use with hemostatic material.

According to another aspect of the present invention, an apparatus for inhibiting blood loss from a puncture site following percutaneous introduction of instrumentation into a vein or artery or a percutaneous biopsy procedure, includes a tube; an elongated member positioned around the tube, the elongated member including a proximal end and a distal end; a dissolvable distal capsule positioned around the tube, the dissolvable distal capsule including a proximal end and a distal end, wherein the proximal end of the dissolvable distal capsule attaches to the distal end of the elongated member; and hemostatic material located inside the dissolvable distal capsule.

According to another aspect of the present invention, a method of providing hemostasis at a blood vessel puncture site in a patient, includes the steps of placing a hemostatic material delivery system over the proximal end of a guidewire extending from a puncture site in a patient's artery, the delivery system including an elongated member having a lumen for receiving the guidewire, a dissolvable distal capsule, and a hemostatic material located inside the dissolvable distal capsule; dissolving the distal capsule; and retracting the elongated member.

According to yet another aspect of the present invention, a system for locating a puncture site in a blood vessel wall and for inhibiting blood loss from the puncture site includes a hemostatic material delivery system having a tube; an elongated member positioned around the tube, a dissolvable distal capsule positioned around the tube, and a hemostatic material located inside the dissolvable distal capsule; and a control tip assembly having a control tip and a control tip body.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIG. 1a is a section of the embodiment shown in FIG. 1.

FIG. 5 is a cross-sectional view of another embodiment of an apparatus for inhibiting blood loss in accordance with the present invention;

DESCRIPTION OF PREFERRED EMBODIMENTS

Figure 1:
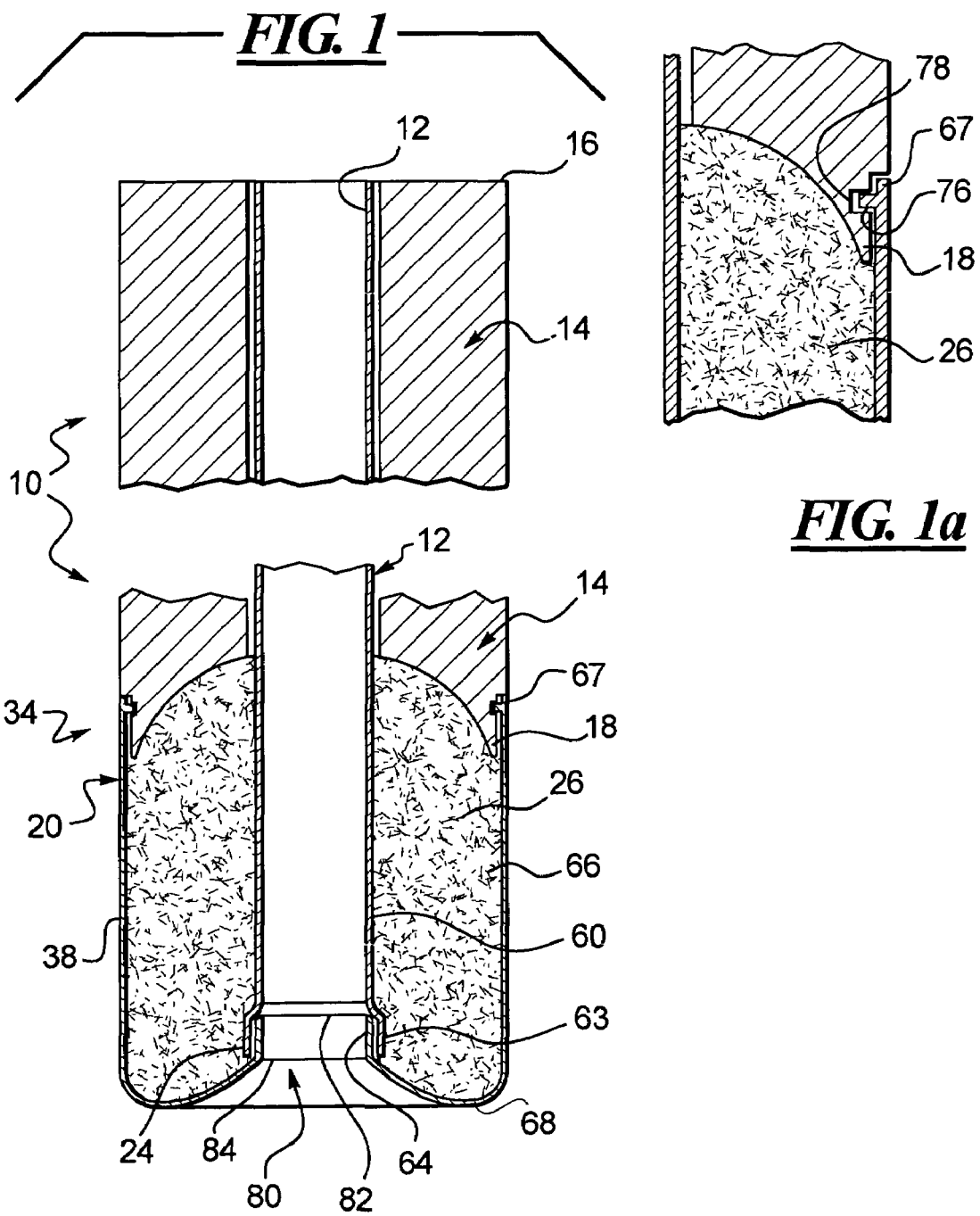
FIG. 1 is a cross-sectional view of the first embodiment of an apparatus for inhibiting blood loss in accordance with the present invention.

Referring to the drawing figures, like reference numerals designate identical or corresponding elements throughout the several figures.

FIG. 1 illustrates an apparatus 10 for locating a puncture site in a blood vessel wall and for inhibiting blood loss from the puncture site according to the present invention. The apparatus 10 includes a tube 12, an elongated member 14, a dissolvable distal capsule 20, and sponge 26 located inside the dissolvable distal capsule 20. The elongated member 14 has a proximal end 16 and a distal end 18, and is positioned around the tube 12. In a preferred embodiment, the distal end of the elongated member 14 has a substantially concave spherical shape. However, it can be appreciated that the distal end 18 of the elongated member 14 can have any concave shape including a rectangular, a stepped or a flat surface which accommodates the sponge 26 located inside the dissolvable distal capsule 20. At the distal end 18 of the elongated member 14, the elongated member 14 has a contact zone 34 in which the elongated member 14 has an outer diameter which is slightly smaller than the outer diameter of the more proximal portion of the elongated member 14 to allow the dissolvable distal capsule 20 to slide onto the contact zone 34 of the elongated member 14. In the preferred embodiment, the inner diameter of the elongated member 14 in the contact zone 34 is equal to the inner diameter of the dissolvable distal capsule 20, and the outer diameter of the distal capsule 20 is equal to the outer diameter of the elongated member 14 proximal to the contact zone 34 to provide a smooth transition from the dissolvable distal capsule 20 to the elongated member 14. The outer diameter of the elongated member 14 proximal to the contact zone 34 is slightly larger than the access sheath or device that occupied the vessel puncture, and preferable 2 Fr larger.

Figure 3:
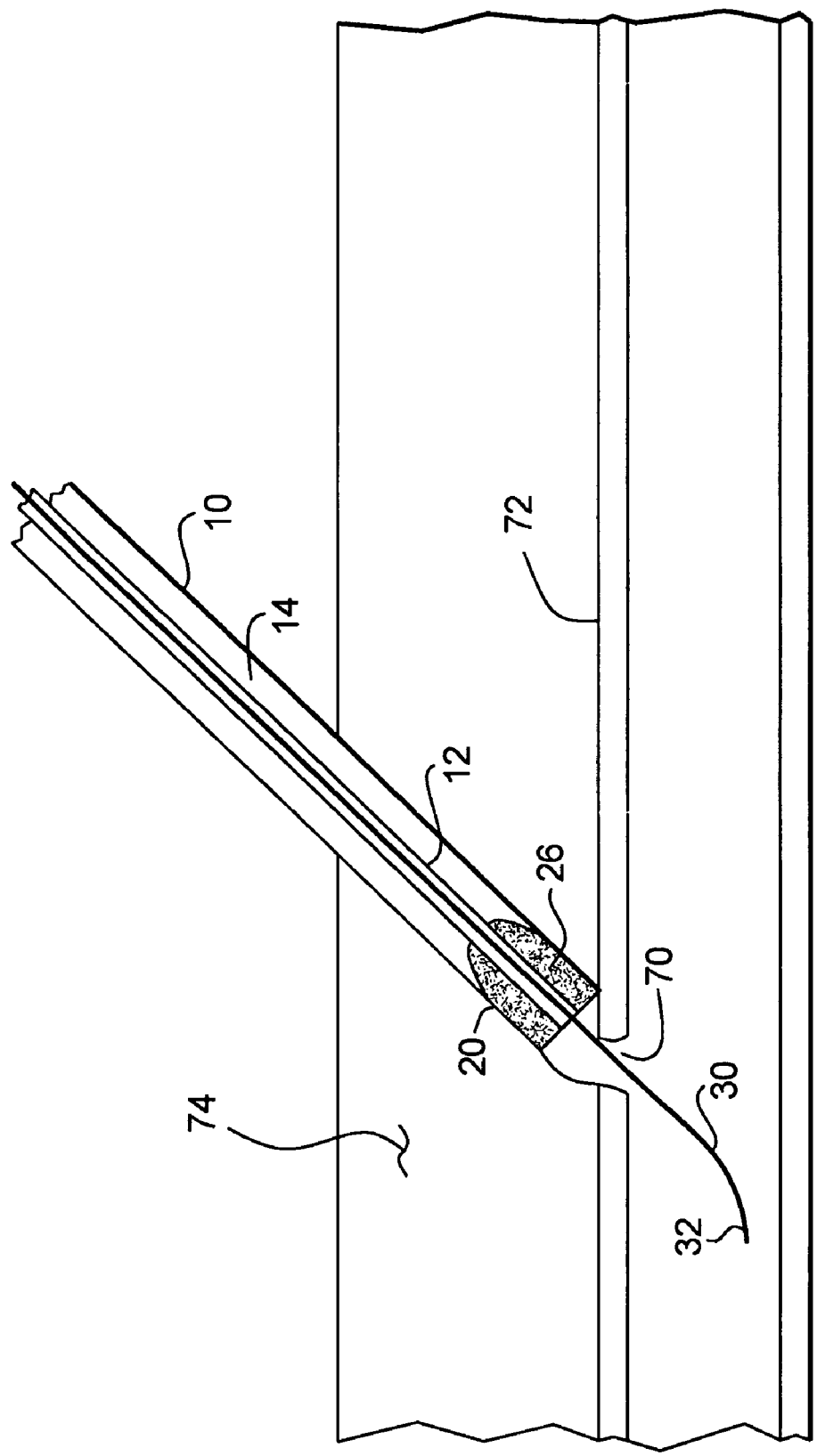
FIG. 3 is a cross-sectional view of a punctured blood vessel and an apparatus for inhibiting blood loss from a puncture site in accordance with the present invention.

The tube 12 has a proximal end 22 and a distal end 24 and extends longitudinally from the proximal end 16 beyond the distal end 18 of the elongated member 14. The tube 12 has an inner diameter of about 0.040 to 0.120 inches, preferably about 0.050 to 0.090 inches, and should loosely accommodate a guidewire 30, as shown in FIG. 3. The tube 12 has a wall thickness of about 0.0005 to 0.005 inches and preferably 0.001 to 0.002 inches. At the distal end 24 of the tube 12, the inner diameter 62 of the tube 12 is slightly greater than the inner diameter 60 of the tube 12 along its proximal portion to accommodate a cylindrical section 80 of the dissolvable distal capsule 20. In a preferred embodiment, the inner diameter 60 of the tube 12 is equal to the inner diameter 64 of the edge of the dissolvable distal capsule 20. For reasons which will be appreciated by those skilled in the art, the tube 12 can optionally be coated or otherwise protected with a material which inhibits blood coagulation. By way of example and not of limitation, the tube 12 can be coated with material including heparin (e.g. heparinized), tPa, or other functionally similar materials or compounds which inhibit or prevent blood from clotting or otherwise coagulating in the tube 12.

The dissolvable distal capsule 20 is positioned around the tube 12, and has a proximal end 67 and a distal end 68. The dissolvable distal capsule 20 and the tube 12 form a coaxial space 66 therebetween for the sponge 26. The proximal end 67 of the dissolvable distal capsule 20 fits snugly around the distal end 18 of the elongated member 14 and can be attached thereto by adhesive or gelatin solution, or by wetting the capsule so that it becomes sticky prior to positioning the capsule 20 around the tube so that the capsule and the tube are bonded to one another. Alternatively, the capsule 20 can be held to the elongated member 14 by frictional engagement or by an interlock system such as an annular ring 76 formed in the capsule 20 and a corresponding annular groove 78 formed in the elongated member 14, as shown in FIG. 1a.

The dissolvable distal capsule 20 includes an outer tubular section having a proximal end 67 and a distal end 68. The proximal end 67 is open, having an inner diameter slightly greater than or equal to the outer diameter 36 of the elongated member 14 at the elongated member's distal end 18. The distal end 68 of the dissolvable distal capsule 20 is rounded to prevent catching on subcutaneous tissue as the apparatus 10 is inserted through the epidermal outer layer and subcutaneous tissue. The distal end of the capsule 20 has cylindrical section 80 for receiving the tube 12. The cylindrical section 80 has a proximal end 82 and a distal end 84, and the outer diameter of the cylindrical section 80 is approximately equal to or slightly smaller than the inner diameter of the tube 12.

The elongated member 14 is preferably a rigid or semi-rigid polymer such as PVC (polyvinyl chloride) or polycarbonate, but may be made of any suitable material, including SST. The tube 12 can be made from any number of polymers or from thin wall SST. The dissolvable distal capsule 20 is made from known absorbable, biocompatible materials, such as gelatin films like Gelfilm (R) from Upjohn or like gel-cap vitamins. Preferably we use gelatin film; preferably the hardness of the gelatin film forming the distal capsule is between about 40 and about 80 on the Shore A scale; and preferably it has a bloom of at least 270, which is normally called "high" bloom. However, in some circumstances the gelatin film could have a hardness and bloom outside these ranges.

The sponge 26 is preferably a liquid permeable, water soluble gelatin based sponge. Other hemostatic material can be used as well, instead of sponge 26, such as fibrillar collagen, collagen sponge, regenerated oxidized cellulose, gelatin powder, or hydrogel particles. Alternatively, the sponge may be composed of an absorbable collagen or other types of absorbable polymers. One type of absorbable sponge material which is acceptable for use in the present invention is Gelfoam™, manufactured by the Pharmacia & Upjohn Company. Gelfoam™ is a porous, pliable, cross-linked gelatin material and is available commercially in sheet form as pre-compressed or non-compressed sponge. Alternatively, the sponge can be made by mixing a suitable organic solvent (e.g., formaldehyde) with an aqueous solution of gelatin. The organic solvent facilitates the cross linkage of gelatin polymers. It is expected that glutaraldehyde may also be suitable. The resulting solution is then incubated typically at slightly above room temperature (30 degree-40 degree C.). Thereafter, the solution is aerated to cause it to foam, and the foam is dried to produce the absorbable sponge material.

Suitable absorbable sponge materials are described in U.S. Pat. No. 2,465,357 which is incorporated herein by reference.

The apparatus 10 may be assembled by placing the tube 12 within the dissolvable distal capsule 20, then compressing the sponge 26 and placing it within the coaxial space 66 between the tube 12 and dissolvable distal capsule 20. The sponge can be compressed to between 90% and 5% of its uncompressed cross-sectional thickness. The elongated member 14 is then placed over the proximal end 22 of the tube 12 and inserted into the dissolvable distal capsule 20 and can be used to apply pressure to further compress the sponge, if desired.

Figure 2:
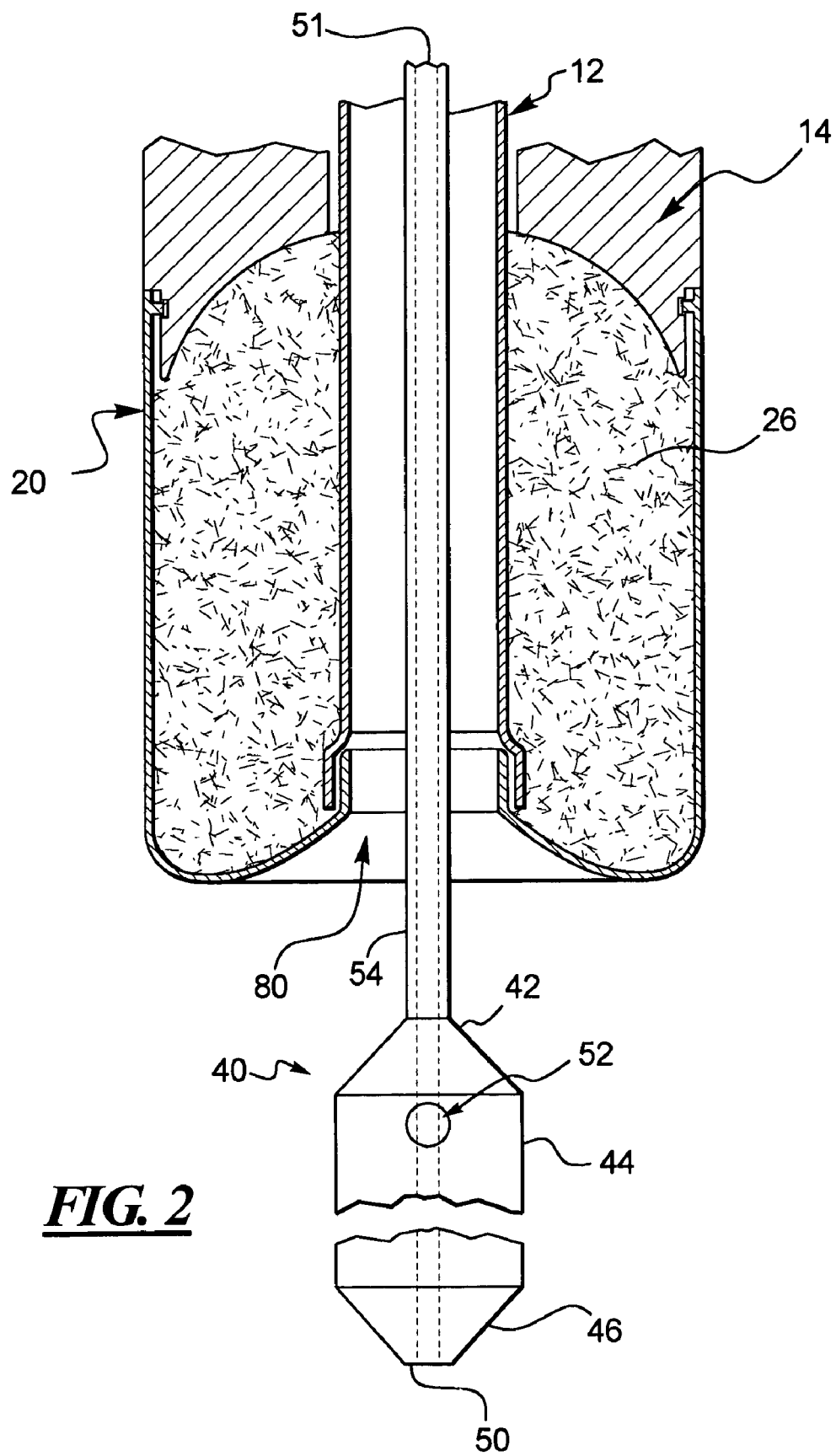
FIG. 2 is a cross-sectional view of the second embodiment of an apparatus for inhibiting blood loss from a puncture site with a control tip assembly in accordance with the present invention.

FIG. 2 illustrates an alternative embodiment of apparatus 10 of FIG. 1 further including a control tip assembly 40. The control tip assembly 40 at its proximal end is mounted to a tube 54. The control tip assembly 40 includes a proximal end portion 42, a distal end 46 portion having a distal port 50, and a central portion 44 between the proximal end portion 42 and the distal end portion 46. The control tip assembly 40 includes a lumen 51 which extends longitudinally between proximal end portion 42 and the distal end portion 46. The lumen also extends through tube 54. For reasons which will be readily appreciated by one of ordinary skill in the art, the lumen 51 can optionally be coated or otherwise provided with an interior surface which inhibits blood coagulation. Further, by way of example and not of limitation, the lumen 51 can be coated with material including heparin (e.g. heparinized), tPa, or other functionally similar materials or compounds which inhibit or prevent blood from clotting or otherwise coagulating in the lumen 51.

As illustrated in FIG. 2, the center portion 44 preferably has a constant outer diameter. The proximal and distal ends are tapered; however, it can be appreciated that the proximal and distal end portions 42 and 46 can alternatively be a step, rounded shoulder, or the like. The control tip assembly 40 also includes a hole 52 which connects the exterior of the control tip assembly 40 with the lumen 51. The lumen 51 has an inner diameter selected to be larger than the external diameter of a guidewire, preferably an exchange wire, used therewith. Furthermore, a plurality of holes (not illustrated) can be formed in the control head, circumferentially spaced and at the same longitudinal location as hole 52.

The proximal and distal portions 42, 46 of the control tip assembly 40 can be relatively thin walled such that the internal dimensions of the lumen 51 in the central portion 44 is larger than in the proximal end portion 42 and distal portion 46 of the control tip assembly 40. As also described briefly above, the distal portion 46 of control tip assembly 40 includes a distal port 50 having an internal opening diameter also selected to be larger, and preferably only slightly larger, than the external diameter of the guidewire 30 used with the control tip assembly. While the function of the distal port 50 in conjunction with a guidewire 30 will be described in greater detail below, one aspect of the present invention is that by selecting the external diameter of guidewire 30 and the inner diameter of the distal port 50 to be only slightly different, blood flow into interior of control tip assembly 40 is greatly restricted, thus allowing the hole 52 to be the sole entrance into the control tip for blood to flow up the lumen 51 to indicate that the control tip assembly 40 has been located in a blood vessel.

Preferably, the control tip assembly is formed of a flexible, biocompatible material, such as a thermoplastic. By way of example and not of limitation, the material out of which the control tip is formed has a Shore hardness between about 98 A-74 D.

For the control tip assembly herein, the outer diameter of the central portion 44 is between about 4 French and about 10 French, preferably between about 6 French and about 8

French. It is preferably equal to or similar in diameter to the access sheath that was used to make the puncture. The length of the control tip assembly, between the distal most end and the proximal end of the proximal end portion 42, should be at least about 1 inch and preferably about 8 inches (6.4 cm), and more preferably about 2 to 4 inches. Control tip assemblies of these dimensions are well suited for controlling puncture sites as described herein, particularly puncture sites used during percutaneous-type vascular access.

FIG. 3 illustrates the operation of the apparatus 10 as shown in FIG. 1. After an endoluminal procedure which has been performed using, in part, a percutaneous access sheath for access to the patient's vasculature, a guidewire 30 is advanced through the sheath, into the patient's blood vessel 72 through a puncture site 70 in the vessel wall, and the sheath is removed. The apparatus 10 is then placed over the guide wire 30 and pushed through the patient's skin. The operator uses the apparatus 10 to locate the desired delivery location by bumping into the artery 72. Once the desired delivery position is achieved, the operator retracts the tube 12 to expose at least part of the sponge 26 to blood from blood vessel 72, which starts the process of sponge expansion. Simultaneously, the dissolvable distal capsule 20 is exposed to blood and begins to soften and dissolve. The dissolvable distal capsule 20 dissolves in about 30 sec. to 10 min. and preferably in about 1 minute. Once the dissolvable distal capsule has dissolved, the sponge 26 is free to expand into the puncture site. The dissolvable distal capsule 20 will also release itself from the elongated member body 14 as a result of softening and dissolving of the capsule. During and after dissolution of the capsule the operator may apply pressure over the site. Then the operator can then apply diffuse external pressure to the tissue over the sponge 26 and remove the guidewire 30 and the elongated member 14.

Figure 4:
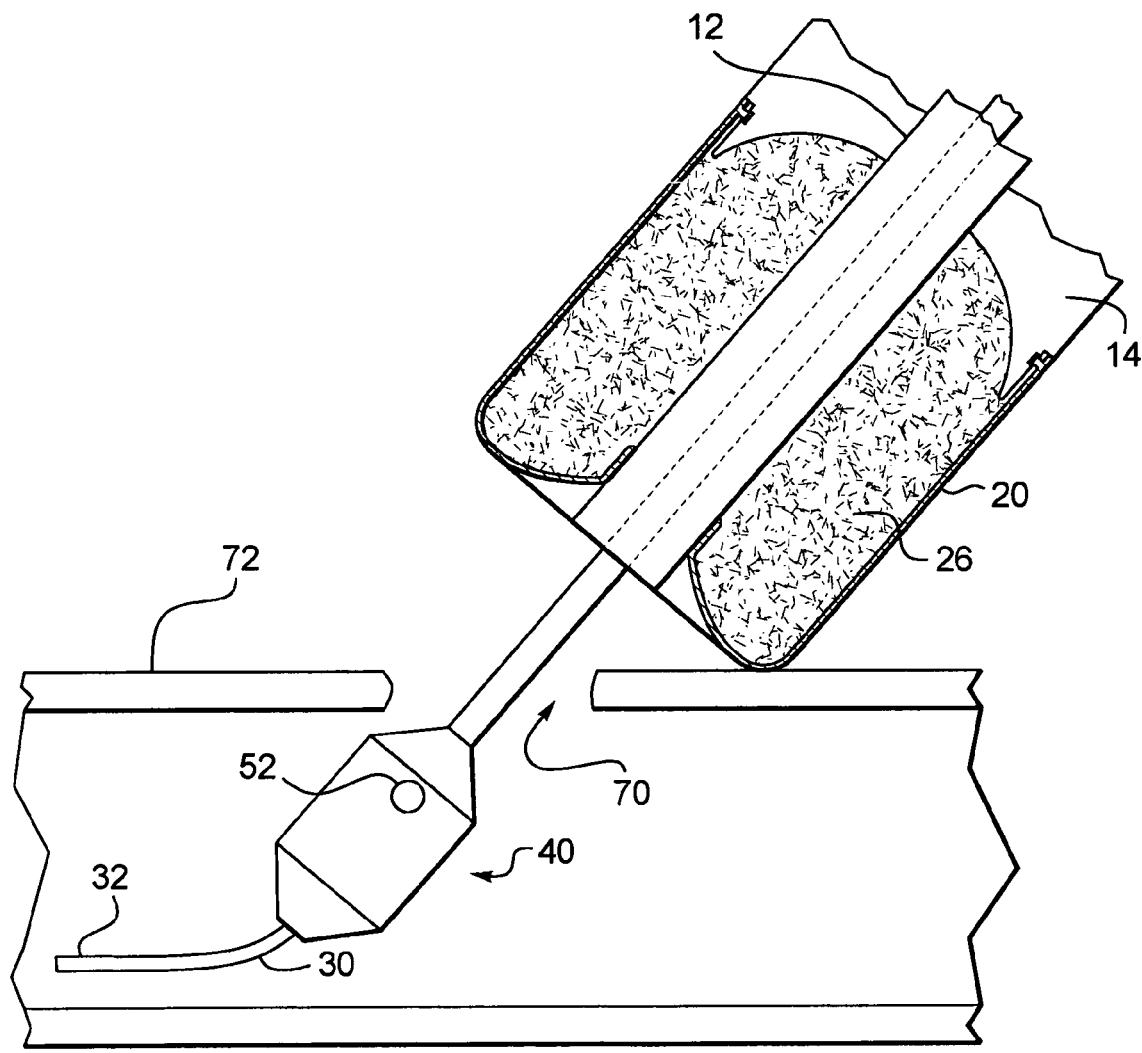
FIG. 4 is a cross-sectional view of a punctured blood vessel and an apparatus for inhibiting blood loss from a puncture site with a control tip assembly (as shown in FIG. 2) in accordance with the present invention.

The use of the FIG. 2 embodiment of apparatus 10 is shown in FIG. 4. The operator places the control tip assembly 40 over the proximal end of the guidewire 30 which extends from the patient's artery and pushes the apparatus through the patient's skin. The apparatus 10 locates the desired location by bumping into the arterial puncture site 70. The control tip assembly 40 provides additional benefits such as hemostasis and bleedback via the bleedback hole 52 or through the tube 54. Once in the desired delivery location, the tube 12 is retracted to expose the sponge 26 from the puncture site 70 and the blood vessel 72. This starts the process of sponge 26 expansion. When the user observes that the bleedback of the tube 54 is diminishing significantly, the control tip assembly 40 can be retracted far enough to control the puncture site 70. As discussed above in connection with FIG. 3, the dissolvable distal capsule 20 softens and dissolves, releasing the sponge 26 into the puncture site and detaching the sponge 26 from the elongated member 14. The control tip assembly 40 is then completely removed from the puncture site 70 and the skin 74. During and after dissolution of the capsule the operator may apply pressure over the site The operator then applies diffuse external pressure to the tissue over the sponge 26 and removes the guidewire, elongated member 14 and tube 12, if it has not already been removed.

In an alternative embodiment illustrated in FIG. 5, the tube 12 shown in FIG. 1 is eliminated. The apparatus 90 includes an elongated member 94 having a lumen 92 for receiving a guidewire 110, a dissolvable distal capsule 100 positioned around the lumen 92 and a sponge 116 located inside the dissolvable distal capsule 100. The lumen 92 (which is defined by the inner surface of the elongated member 94) for receiving the guidewire 110 extends from a proximal end 96 of the elongated member 94 to a distal end 98 of the elongated member 94. A dissolvable distal capsule 100 attaches to the distal end 98 of the elongated member 94 as described above. In this embodiment the dissolvable capsule includes an inner cylindrical portion 102 that extends approximately the same length as the outer cylindrical portion 104 and into at least a portion of the elongated member 94. The capsule has a rounded end 106 extending between the inner cylindrical portion 102 and the outer cylindrical portion 104.

In operation, the apparatus 90 as shown in FIG. 5 is placed over the proximal end 112 of a guidewire 110 extending from a patient's artery and the apparatus 90 is advanced into the patient. The apparatus 90 locates the desired delivery location by bumping into the arterial puncture site to obtain the desired delivery position. This starts the process of sponge 116 expansion, wherein the dissolvable distal capsule 100 begins to soften and dissolve rapidly. Once the dissolvable distal capsule 100 has dissolved, the sponge 116 is free to expand into the puncture site and secure itself within the puncture site. The dissolvable distal capsule 100 will also release itself from the elongated member 94 body as a result of softening and dissolving of the dissolvable distal capsule 100.

Figures 6, 7:
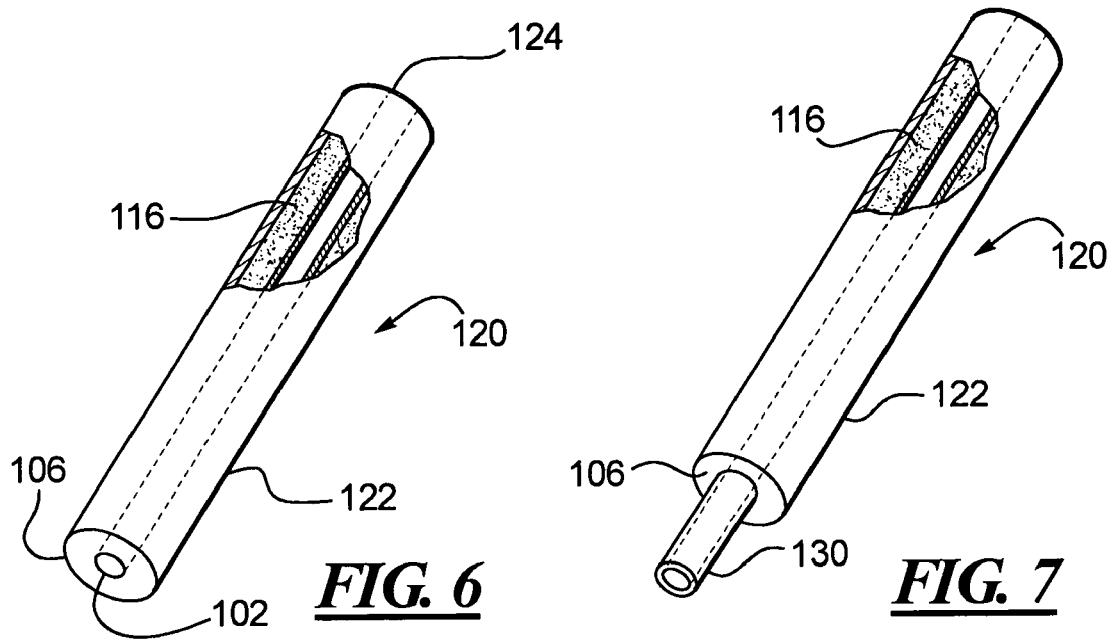
FIG. 6 is another embodiment of the device in accordance with the present invention.
FIG. 7 is an embodiment of the device of the present invention including a retention tip.

FIG. 6 illustrates another embodiment of the present invention. This embodiment shows a hemostasis device 120 including a dissolvable capsule 122 substantially the same as the distal capsule 100 shown in FIG. 5, with the exception that the hemostasis device of this embodiment is not designed to be connected to an elongated member such as the elongated member 94 shown in FIG. 5. In the embodiment of FIG. 6 the proximal end 124 of the capsule 122 can be open, or it can be closed as is the rounded end 106.

FIG. 7 illustrates another embodiment similar to the embodiment in FIG. 6. However, in the FIG. 7 embodiment a retention tip 130 is affixed to the rounded end 106. The retention tip is substantially cylindrical and the central lumen of the retention tip 130 is coaxial with the lumen of the dissolvable capsule 122.

Figure 8:
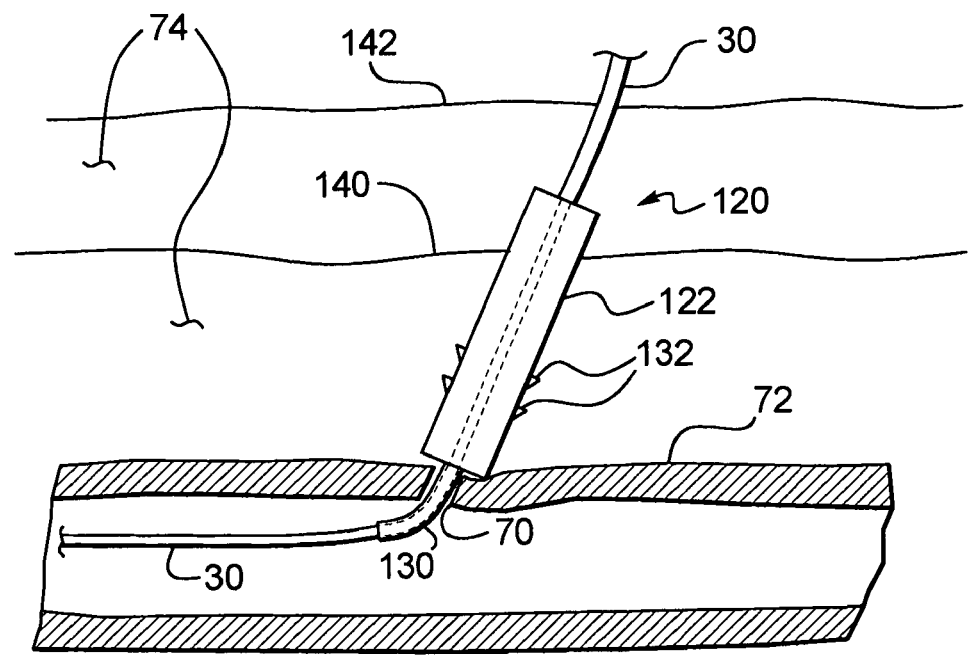
FIG. 8 is a cross-sectional view of a punctured blood vessel and an apparatus for inhibiting blood loss from a puncture site using the device shown in FIG. 7.

FIG. 8 shows another embodiment, which is similar to the embodiment in FIG. 7. However, in the FIG. 8 embodiment a plurality of retention anchors 132 are provided on the capsule 122. The retention anchors 132 consist of one or more ridges formed around the circumference of the capsule 122, and their function will be described below.

As shown in FIG. 8, the hemostasis device 120 is inserted into the patient's skin 74. During the insertion procedure the operator uses the retention tip 130 to help maintain the hemostasis device 120 at its proper location relative to the puncture site 70. Also, the retention anchors 132 help keep the device located in the proper position while the operator removes the wire 30 and thereafter until the device has dissolved. The operator may insert the hemostasis device so that it extends above the surface of the patient's skin 140 or can push it below the surface of the patient's skin 142.

Figures 9, 10:
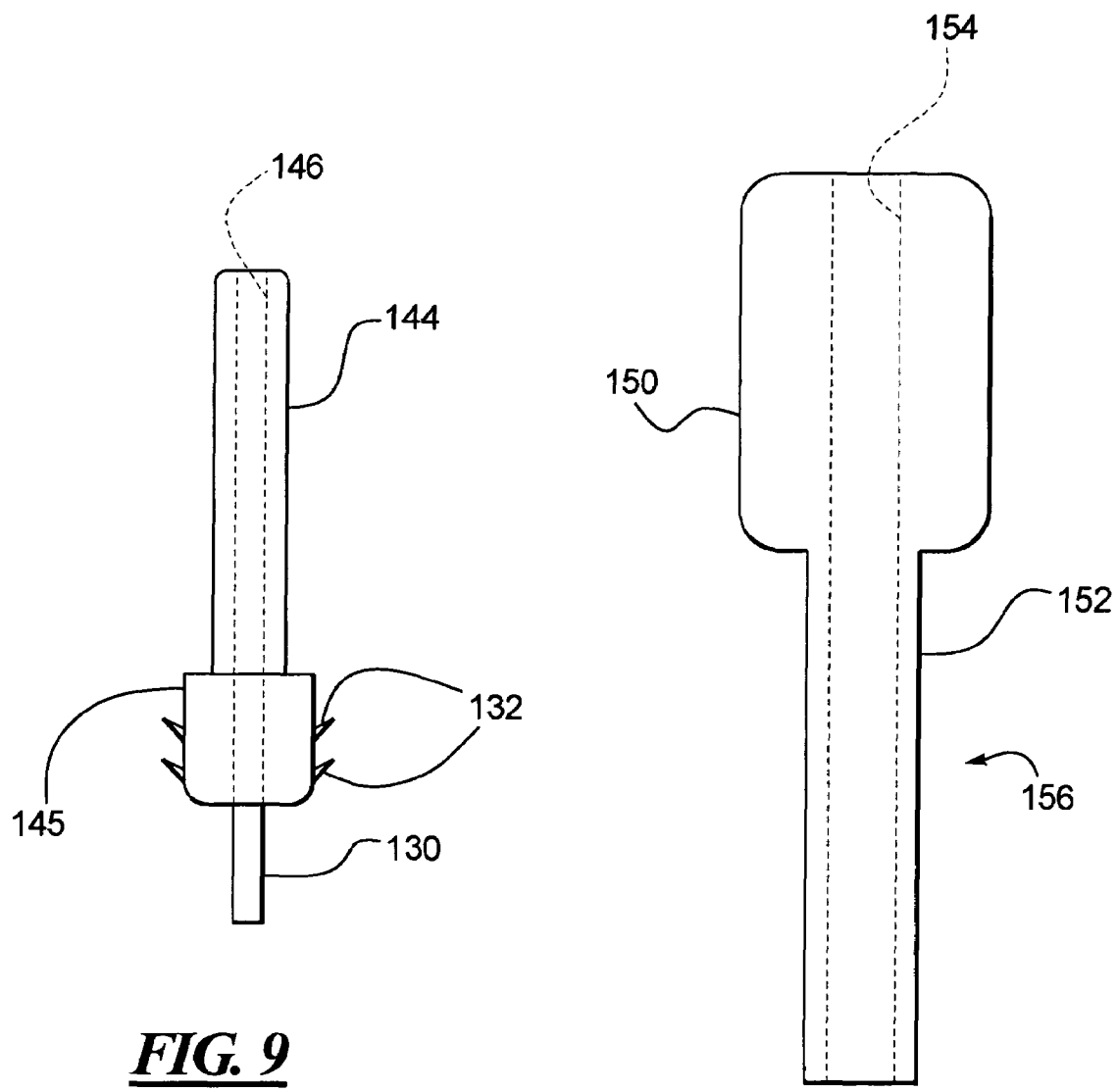
FIG. 9 is another embodiment of a device according to the present invention.
FIG. 10 is another embodiment of a device according to the present invention.

FIG. 9 shows another embodiment. In this embodiment a proximal dissolvable capsule 144 is affixed to the proximal end of a distal dissolvable capsule 145. Both dissolvable capsules 144 and 145 contain compressed sponge which is not shown for the purpose of clarity. In this embodiment, the proximal dissolvable capsule 144 has a diameter smaller than the diameter of the distal dissolvable capsule 145. A lumen 146 extends through the device.

FIG. 10 shows a placement device 156 to aid in the insertion and placement of a hemostasis device shown in FIG. 9. The placement device includes a cylindrical handle 150 and a cylindrical column 152 affixed to the distal end of the handle. A lumen 154 is located axially through the handle 150 and column 152.

Figure 11:
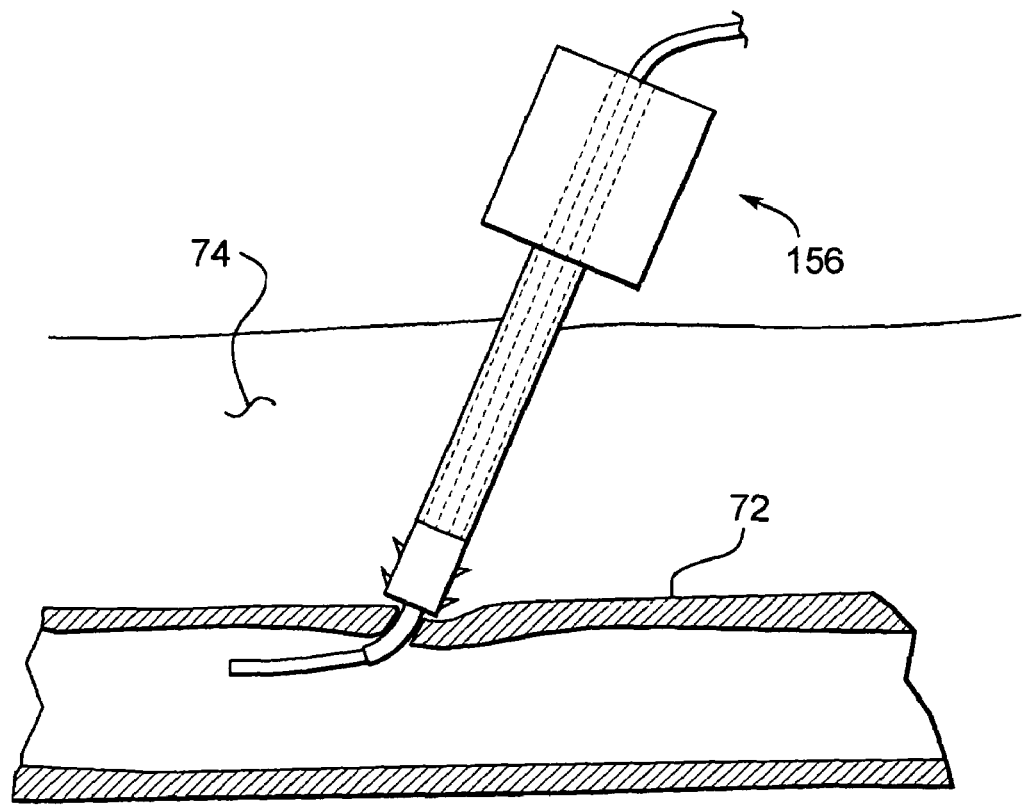
FIG. 11 is a cross-sectional view of a punctured blood vessel and an apparatus for inhibiting blood loss from a puncture site using the device shown in FIG. 10.
Figure 12:
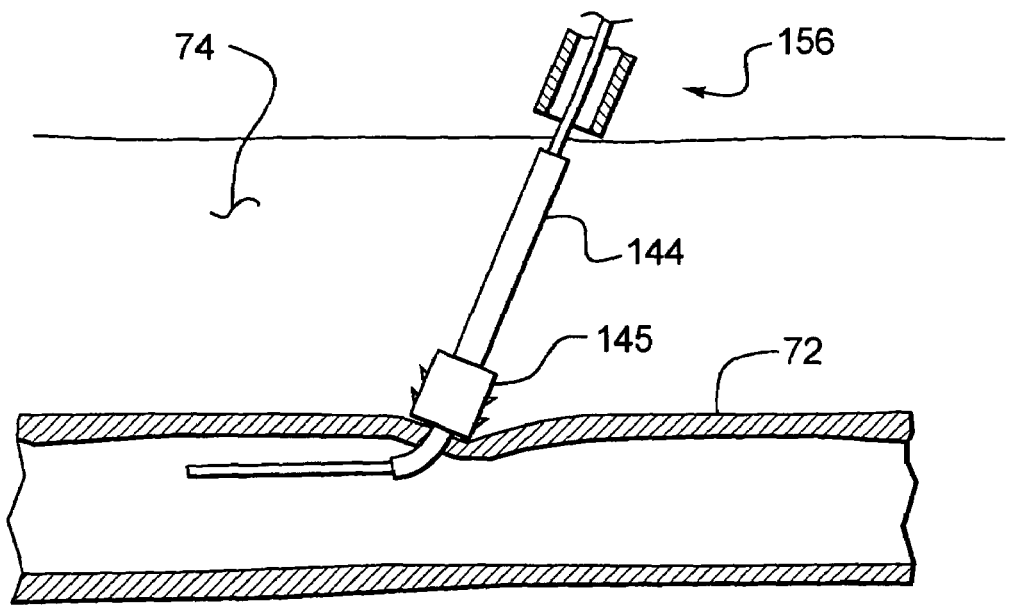
FIG. 12 is a cross-sectional view of a punctured blood vessel and an apparatus for inhibiting blood loss from a puncture site using the device shown in FIG. 9

FIGS. 11 and 12 illustrate the operation of the devices of FIGS. 9 and 10. In this embodiment the hemostasis device of FIG. 9 is inserted into the lumen of the placement device until the proximal part of the distal capsule 145 contacts the distal end of the column 152. Then the wire 30 is inserted through the lumen 146 of the device of FIG. 9 and the operator uses the handle to push the hemostasis device through the patient's skin until the distal dissolvable capsule 145 contacts the outer surface of the blood vessel 72. Then the operator retracts the placement device 156, leaving the hemostasis device in place as shown in FIG. 12. The guide wire can be removed before or after removal of the placement device 156.

Figure 13:
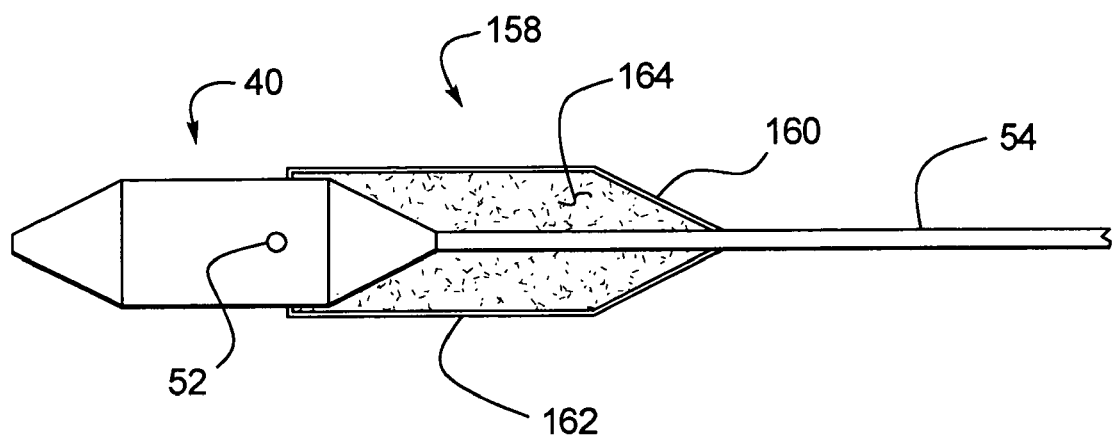
FIG. 13 is another embodiment of a device according to the present invention.

FIG. 13 illustrates another embodiment. This embodiment includes a control tip assembly 40 as shown in FIG. 2 and described above. A proximal gelatin capsule 158 is connected to the control tip 40 assembly proximally thereof. The proximal gelatin capsule 158 consists of a truncated cone-shaped portion 160 and a cylindrical portion 162 connected to the distal end of the cone-shaped portion, both of which are constructed of the same material as the dissolvable distal capsule 20, e.g. gelatin. Located within the proximal gelatin capsule 158 is a compressed sponge 164 which is formed of the same material as sponge 26. The proximal gelatin capsule 158 includes cylindrical openings at each end to fit snugly over the control tip 40 and snugly over the tube 54 so when an operator pushes the device through a patient's skin there is minimal frictional resistance between the leading edge of the proximal gelatin capsule 158 and the skin. Furthermore, the compressed sponge 164 can be packed tightly against the tube 54 and control tip assembly 40 to provide friction therebetween so that that proximal gelatin capsule 158 remains in place when the operator pushes the device through the patient's skin. Alternatively, the control tip assembly 40 and proximal gelatin capsule 158 may be inserted through a procedural access sheath which is already in place.

Figure 14:
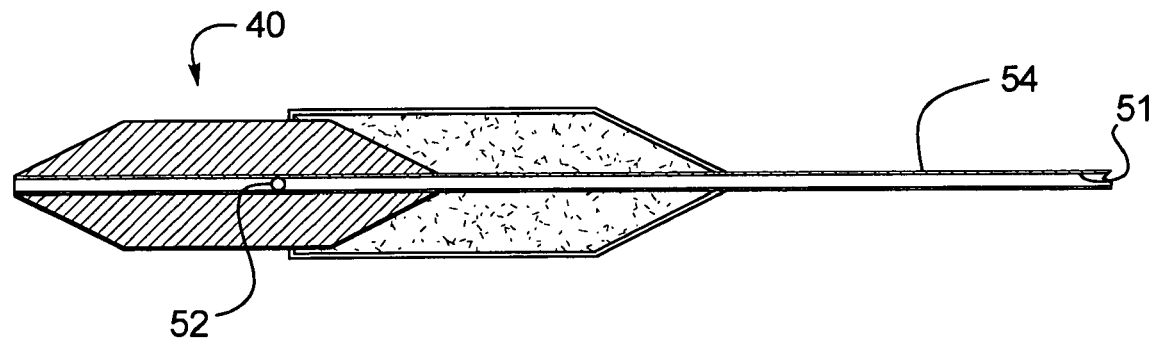
FIG. 14 is another embodiment of a device according to the present invention.

The embodiment shown in FIG. 14 is similar to the embodiment shown in FIG. 13, with the exception that the control tip assembly 40 is formed of rapidly dissolvable material such as the material of the dissolvable distal capsule 20, described above with reference to FIG. 1.

In operation of the embodiments of FIGS. 13 and 14, an operator inserts the devices through a patient's skin in the same manner as the embodiments described above. When bodily fluid contacts the proximal gelatin capsule the capsule dissolves thereby releasing the compressed sponge 164 which provides hemostasis.

Figure 14A:
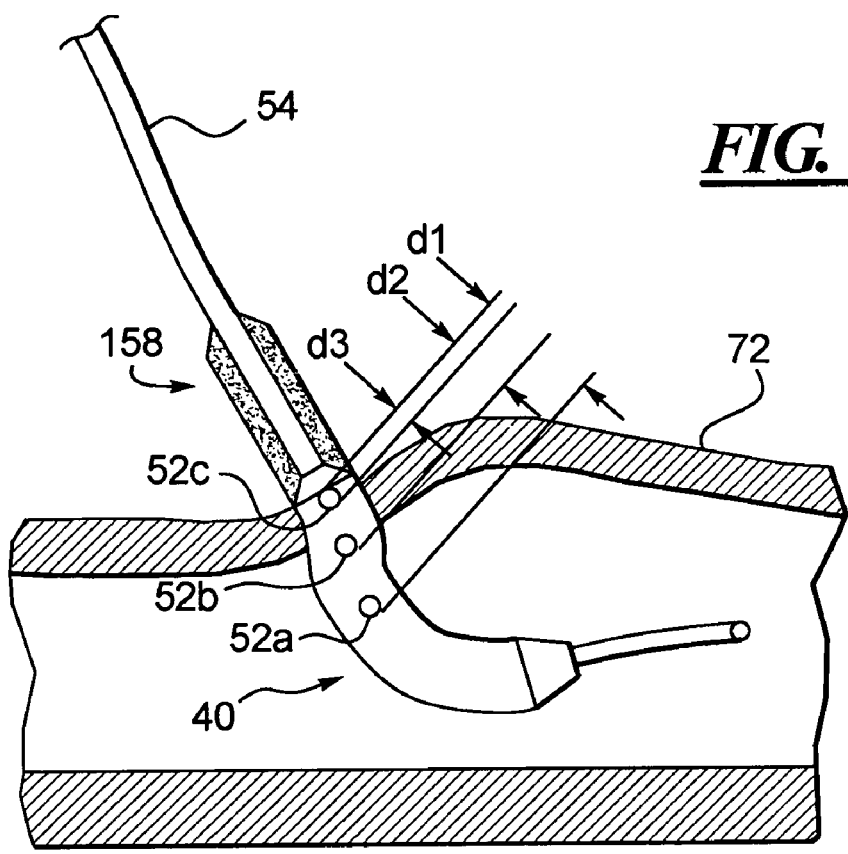
FIG. 14a is another embodiment of a device according to the present invention.

FIG. 14a shows an embodiment where the distance from the distal end of the proximal gelatin capsule 158 to the hole 52 is located at one of three alternative positions, 52a, 52b or 52c. Position 52a is chosen so that when the assembly 188 is pushed in and the operator is first able to observe bleed back due to blood from inside the vessel 72 entering the hole 52, the device is properly positioned. In this example, position 52a is chosen so that the hole 52a is located a distance of d1 from the distal end of the proximal gelatin capsule 158 so that the hemostatic material is released just outside the vessel. Alternatively, bleed back hole 52b is used, which is positioned at d2 where d2 is less than d1 such that the assembly 188 is pushed in until bleed back indication occurs and then withdrawn until bleed back indication first stops in which case the device is properly positioned. In this example d2 is chosen to position the hemostatic material just outside the vessel. Alternatively the bleed back hole 52c may be used, which is positioned at d3 where d3 is less than d2 so that the assembly 188 is pushed in until bleed back indication occurs and then withdrawn until bleed back first stops and then withdrawn an additional predetermined distance. In the example shown d3 and the predetermined distance are chosen to position the hemostatic material just outside the vessel.

Figure 14B:
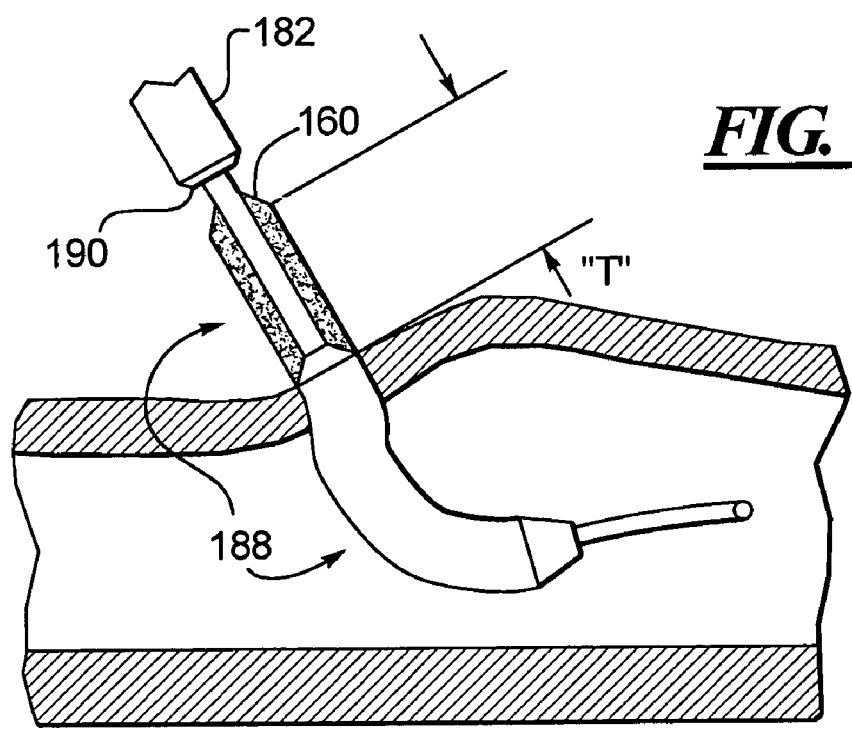
FIG. 14b is another embodiment of a device according to the present invention.

For the embodiments shown in FIGS. 13, 14 and 14a the portion of the tube 54 extending proximally of the proximal gelatin capsule 158 may have a diameter smaller than the control tip 40 or equal to the control tip 40. If the tube 54 is smaller than the control tip 40 and the control tip outside diameter is equal to or slightly smaller than the inside diameter of the access sheath 182, the capsule may be positioned as shown in FIG. 14b. Starting with the sheath already extending into a vessel 72, the assembly 188 is pushed in through the sheath 182 until the cylindrical portion 162 extends distally of the distal end 190 of the sheath 182 and bleed back indication is observed via blood entering the distal end 190 of the sheath. The assembly 188 and sheath 182 are then withdrawn as one until bleed back indication first stops. The sheath 182 and assembly 188 are then withdrawn an "additional distance" to properly position the hemostatic material. In FIG. 14b the "additional distance" is equal to "T", the length of the proximal capsule 158, excluding the length of the cylindrical portion 162 thereof.

Figure 15:
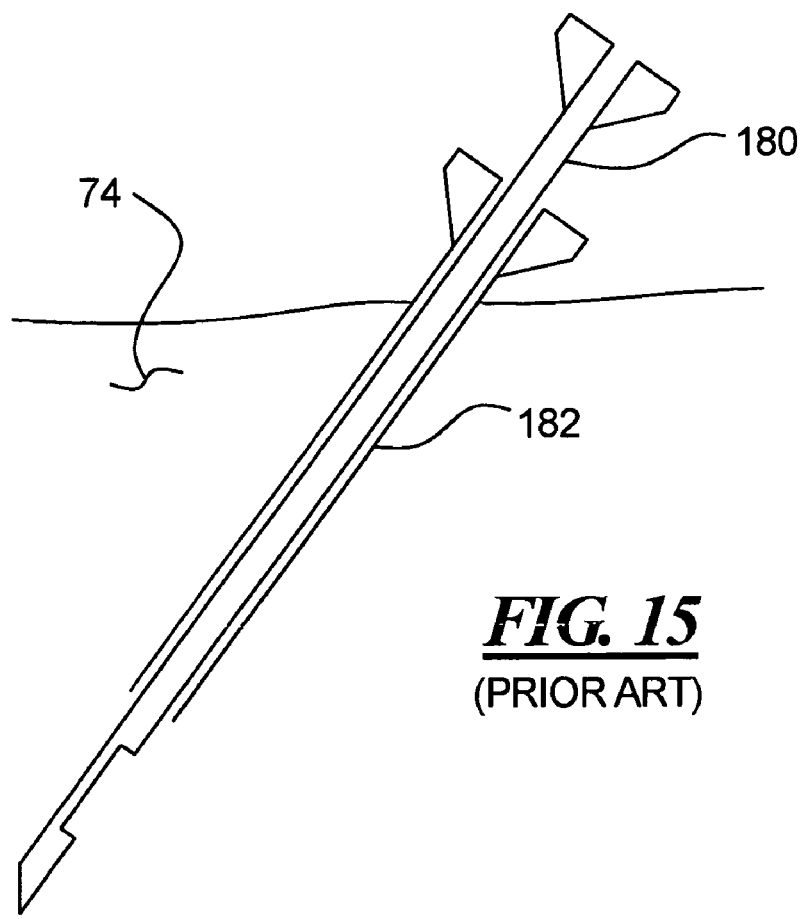
FIG. 15 is a conventional biopsy device shown in use.
Figure 16:
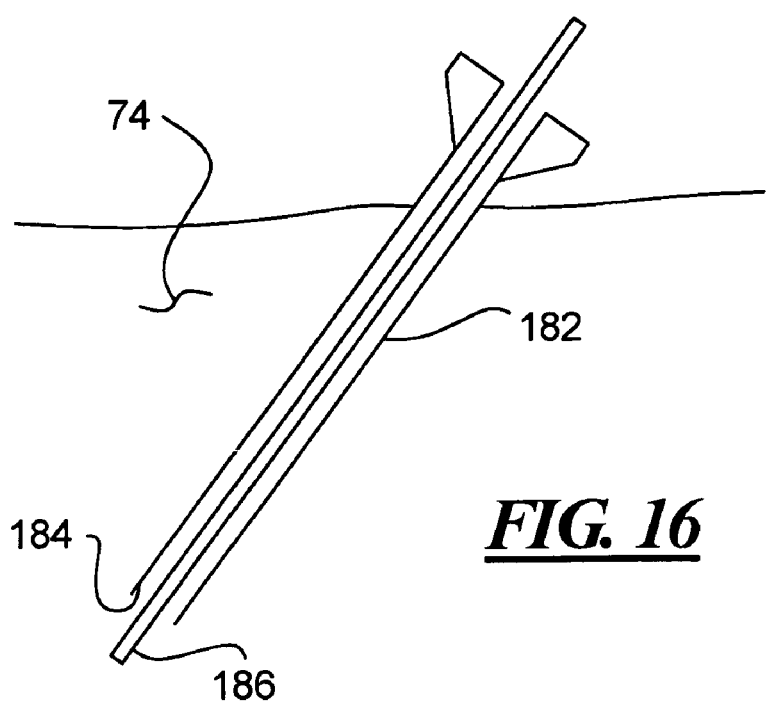
FIG. 16 is another embodiment of a device according to the present invention as used following a biopsy procedure.

FIG. 15 illustrates a conventional biopsy device, including a needle 180 and a guide 182 which has a lumen 184. After the operator collects a tissue sample with the needle 180 the needle is removed, leaving the guide 182 in place. As shown in FIG. 16 the operator then inserts a hemostasis device 186 through the guide 182. The hemostasis device 186 can be formed by rolling a sheet of sponge material tightly to form a cylinder and coating the cylinder with gelatin. Optionally, before rolling the sponge material the operator can moisten the surface of the sponge with distilled water so that the surface dissolves slightly and the sponge sticks to itself and retains its rolled configuration. The operator can then coat the cylindrically formed sponge with a gelatin solution, preferably 5% plus or minus 0.5%, or the operator can insert the cylindrically-formed sponge into a pre-formed gelatin capsule having the appropriate cylindrical shape. The operator can insert the hemostasis device 186 so that it extends beyond the distal end of the guide 182 so that the hemostasis device 186 contacts the patient's blood and dissolves to create hemostasis. The operator can remove the guide 182 partially or completely at the appropriate time as the hemostasis device 186 is dissolving.

Figure 17:
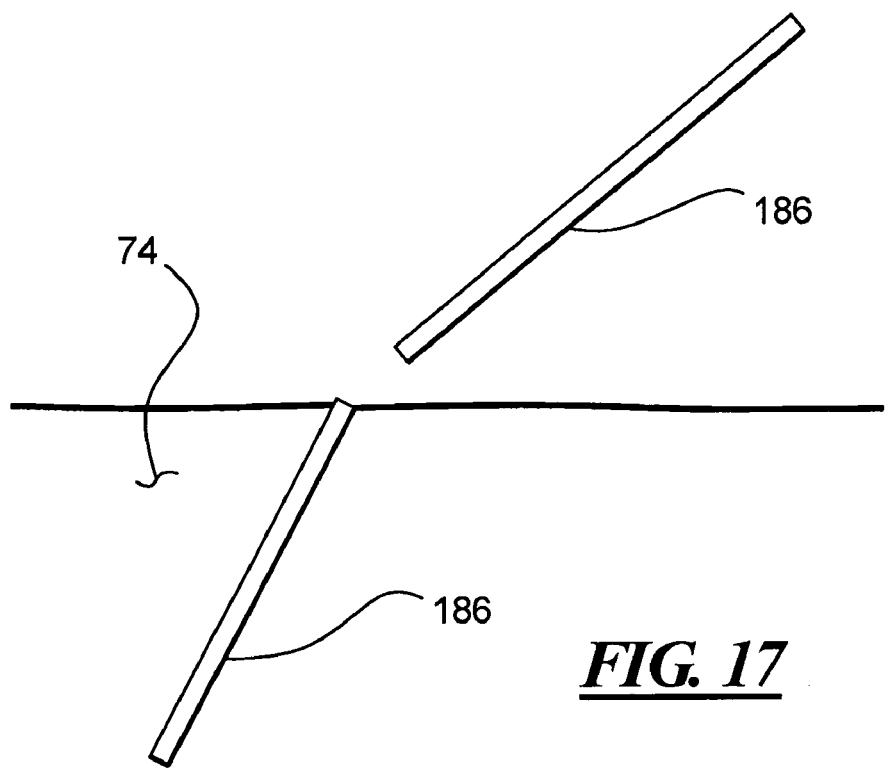
FIG. 17 is another embodiment of a device according to the present invention as used following a biopsy procedure.
Figure 18:
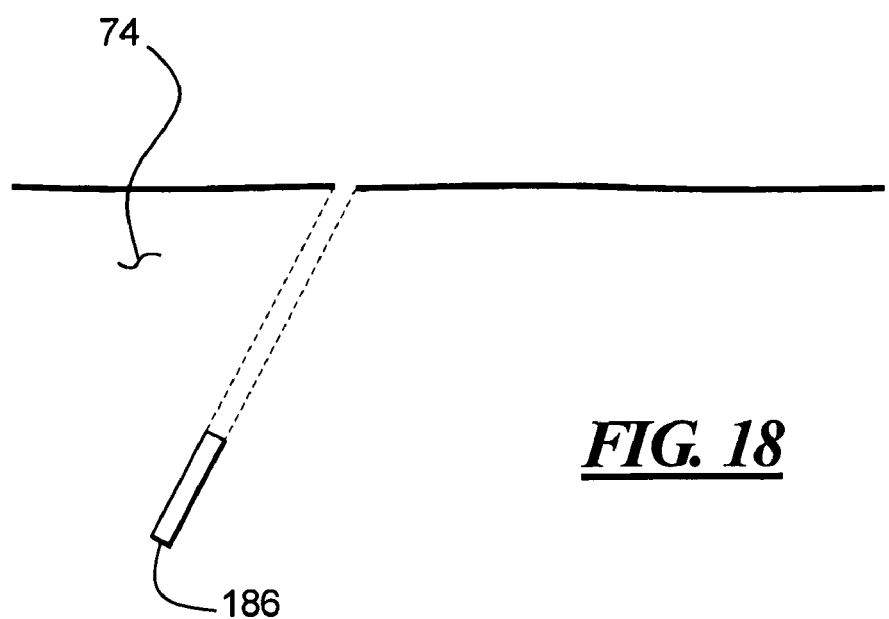
FIG. 18 is another embodiment of a device according to the present invention as used following a biopsy procedure.

FIG. 17 illustrates another embodiment wherein the operator of the biopsy device completely removes the guide 182 without inserting the hemostasis device 186. The operator then inserts the hemostasis device into the patient's skin 74. If the hemostasis device is sufficiently long so that when it is completely inserted, a portion remains above the skin surface, the portion remaining above the skin surface can be trimmed off flush with or below the skin surface. Alternatively, as shown in FIG. 18 the hemostasis device can be shorter than the depth of the wound in the patient's skin, in which case the operator can push the homeostasis device 186 below the surface of the patient's skin with an appropriate tool such as a rod.

It should be understood that the hemostasis device 186 which is formed by inserting a sponge into a pre-formed gelatin capsule can have alternative configurations which are beneficial. Likewise, the dissolvable distal capsule 20

(FIGS. 1-4), the dissolvable distal capsule 100 (FIG. 5), the dissolvable capsule 122 (FIGS. 6-8), the distal capsule (FIGS. 9-12), and the proximal gelatin capsule 158 (FIGS. 13-14b) can have similar alternative configurations which are beneficial. These alternative, beneficial configurations have similarities to each other, and therefore preferred alternative configurations of hemostasis device 186 will be described below, and it should be understood that similar configurations of the other capsules can be readily understood by one skilled in the art.

Figure 19:
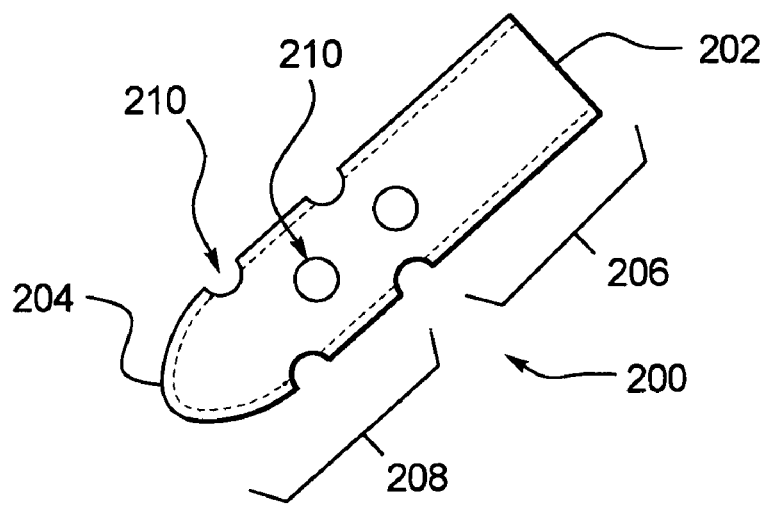
FIGS. 19-21 are other preferred embodiments of the dissolvable capsule of a hemostasis device.
Figure 20:
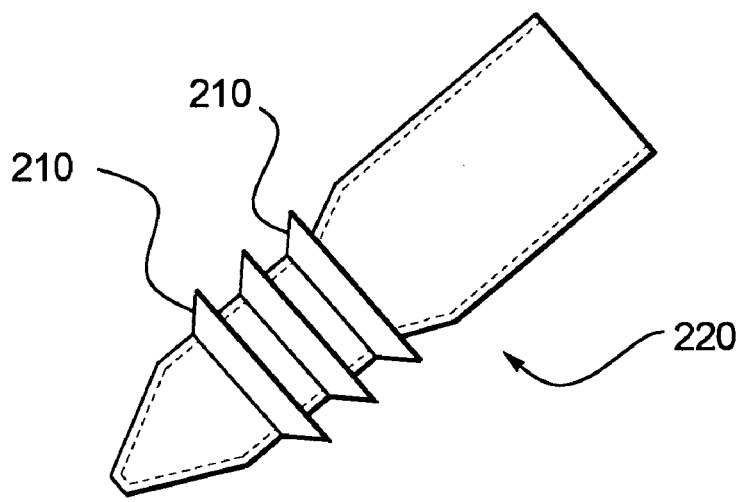
Figure 21:
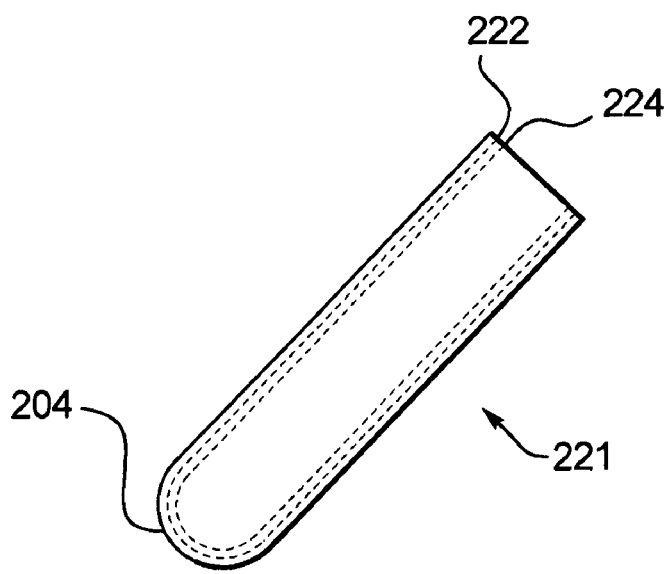

Turning now to FIGS. 19-21, preferred embodiments of the dissolvable capsule of a hemostasis device are shown. It should be understood that the capsules can be, e.g. a dissolvable distal capsule which can be used in place of the dissolvable distal capsule 20 (FIGS. 1-4), a dissolvable distal capsule which can be used in place of the dissolvable distal capsule 100 (FIG. 5), a dissolvable capsule which can be used in place of the dissolvable capsule 122 (FIGS. 6-8), a distal capsule which can be used in place of the distal capsule (FIGS. 9-12), or a capsule which can be used in place of the proximal gelatin capsule 158 (FIGS. 13-14b). It should be recognized that in some of these embodiments it may be necessary to modify the configuration of the capsules shown in FIGS. 19-21 for the particular application. For example, the capsule shown in FIG. 19 would be modified to include a cylindrical section 80 and a proximal end 82 in the shape of capsule 20 illustrated in FIG. 1.

In FIG. 19 the capsule 200 is substantially cylindrical and has an open proximal end 202 and a closed distal end 204, and proximal region 206 and distal region 208 are indicated. Hemostasis material such as sponge 26 is located inside the capsule but is not shown for the purpose of clarity. Sponge (or other hemostasis material) can reside within the entire inside of the capsule, or the sponge may occupy only preferred radial and/or axial regions. For instance, the distal region may be vacant, and the proximal region may be occupied by sponge. The proximal portion of the proximal region may be vacant, allowing the inside diameter of the proximal capsule to interact with a placement device. A central radius along the capsule length may be vacant, while other radial regions of the capsule are occupied by sponge, defining a lumen. The distal end may also be provided with a hole, such as a guide wire hole.

In one preferred configuration the capsule includes a plurality of holes 210 as indicated in FIG. 19.

Capsules 200 may be advantageously made from gelatin and formulated to have flexibility (like a gel-cap vitamin E) or to be stiff like a typical 2-piece oral capsule. Capsules are made to dissolve within a predetermined time, with a dissolution time between 10 seconds and 10 days, and normally between one minute and 10 minutes. Also, capsules can be formulated to be inert (e.g. non thrombogenic, not-bacteriostatic) or to provide/deliver therapeutic benefit (e.g. clot acceleration, bacteriostatic). The capsule 200 can vary in characteristics along its length. For example, the distal region can be inert while the proximal region comprises therapeutic material.

A capsule with inert and therapeutic regions can be made by dipping a mandrel having the shape of the inside of the capsule in a gelatin solution having no therapeutic agents. The proximal region only is then dipped in a gelatin solution containing therapeutic agent. These agents may include clot accelerators such as thrombin, calcium based compounds, chitosan, and may also include antibiotics or radiopaque substances.

Turning to FIG. 20, the distal portion 208 of capsule 220 includes ridges to create axial tension so as to secure the capsule in a desired location during and/or post deployment. In other words, distal tension can help pull device off of, i.e. away from or out of a delivery device such as a guide, sheath, or off of a guidewire or catheter body or small diameter tube during delivery device removal. Distal region tension can prevent movement of capsule and sponge against blood pressure or patient movement or external pressure. This feature of axial tension is discussed above with regard to FIGS. 8-12 in which the hemostasis device 120 and distal capsule 145 comprise retention anchors 132.

Turing to FIG. 21, the capsule 221 comprises an outer skin 222 made of inert material and an inner skin 224 which contains a therapeutic agent such as thrombin.

While the invention has been described in detail with reference to preferred embodiments thereof, it will be apparent to one skilled in the art that various changes can be made, and equivalents employed, without departing from the scope of the invention. All of the aforementioned documents are incorporated by reference in each of their entireties herein.

What is claimed is:

1. An apparatus for inhibiting blood loss from a puncture site, the apparatus comprising:
   an elongated tubular member including a proximal end and a distal end with a maximum outer diameter at the distal end,
   a dissolvable tubular capsule including a proximal end and a distal end and a maximum outer diameter between the proximal and distal ends, the proximal end of the capsule being mounted to the distal end of the elongated member, the capsule including an outer skin made of inert material and an inner skin comprising a clot accelerating therapeutic agent,
   a tubular hemostasis material disposed within the dissolvable tubular capsule,
   the dissolvable tubular capsule comprising a plurality of holes disposed in an outer sidewall thereof,
   the elongated member, capsule, and hemostasis material defining a common lumen extending from the proximal end of the elongated member and through the distal end of the capsule, and
   the maximum outer diameter of the distal end of the tubular member being about equal to the maximum outer diameter of the capsule.

2. The apparatus of claim 1 wherein the hemostasis material comprises gelatin.

3. The apparatus of claim 1 wherein the hemostasis material comprises gelatin foam sponge.

4. The apparatus of claim 1 wherein the capsule comprises gelatin.

5. The apparatus of claim 1 wherein the distal end of the capsule is inert and the proximal end of the capsule comprises a clot accelerating therapeutic agent.

6. The apparatus of claim 1 wherein the capsule dissolves after a predetermined time.

7. An apparatus for inhibiting blood loss from a puncture site, the apparatus comprising:
   an elongated tubular member including a proximal end and a distal end with a maximum outer diameter at the distal end,
   a dissolvable tubular capsule including a proximal end and a distal end and a maximum outer diameter between the proximal and distal ends, the proximal end of the capsule being mounted to the distal end of the elongated member,
   a tubular hemostasis material disposed within the dissolvable tubular capsule, the dissolvable tubular capsule comprising a plurality of holes disposed in an outer sidewall thereof, wherein the outer sidewall of the capsule comprises at least one peripheral ridge that acts as an anchoring barb prior to dissolving, the elongated member, capsule, and hemostasis material defining a common lumen extending from the proximal end of the elongated member and through the distal end of the capsule, and the maximum outer diameter of the distal end of the tubular member being about equal to the maximum outer diameter of the capsule.

8. The apparatus of claim 7 wherein the outer sidewall capsule comprises a plurality of peripheral ridges axially spaced apart.

9. An apparatus for inhibiting blood loss from a puncture site, the apparatus comprising:

an elongated tubular member including a proximal end and a distal end with a maximum outer diameter at the distal end, a dissolvable tubular capsule including a proximal end and a distal end and a maximum outer diameter between the proximal and distal ends, the proximal end of the capsule being mounted to the distal end of the elongated member, a tubular hemostasis material disposed within the dissolvable tubular capsule, the dissolvable capsule comprising at least one peripheral ridge disposed in an outer sidewall thereof that acts as an anchoring barb prior to the capsule dissolving, the elongated member, capsule, and hemostasis material defining a common lumen extending from the proximal end of the elongated member and through the distal end of the capsule, and the maximum outer diameter of the distal end of the tubular member being about equal to the maximum outer diameter of the capsule.

10. The apparatus of claim 9 wherein the hemostasis material comprises gelatin.

11. The apparatus of claim 9 wherein the hemostasis material comprises gelatin foam sponge.

12. The apparatus of claim 9 wherein the capsule comprises gelatin.

13. The apparatus of claim 9 wherein the distal end of the capsule is inert and the proximal end of the capsule comprises a clot accelerating therapeutic agent.

14. The apparatus of claim 9 wherein the capsule comprises an outer skin made of inert material and an inner skin comprising a clot accelerating therapeutic agent.

15. The apparatus of claim 9 wherein the capsule dissolves after a predetermined time.

16. The apparatus of claim 9 wherein the outer sidewall of capsule comprises a plurality of axially spaced apart peripheral ridges that act as anchoring barbs prior to dissolving.

17. The apparatus of claim 9 wherein the outer sidewall capsule comprises a plurality of holes.

18. An apparatus for inhibiting blood loss from a puncture site, the apparatus comprising:

an elongated tubular member including a proximal end and a distal end, a dissolvable capsule including a proximal end and a distal end, the proximal end of the capsule being mounted to the distal end of the elongated member, the capsule comprising an outer skin made of inert material and an inner skin comprising a clot accelerating therapeutic agent, a hemostasis material disposed within the dissolvable capsule, the dissolvable capsule comprising a plurality of holes disposed in an outer sidewall thereof, the elongated member, capsule, and hemostasis material defining a common lumen extending from the proximal end of the elongated member and through the distal end of the capsule, and outer radii of the tubular member and capsule being generally uniform and in general matching registry.

19. The apparatus of claim 18 wherein the hemostasis material comprises gelatin.

20. The apparatus of claim 18 wherein the hemostasis material comprises gelatin foam sponge.

21. The apparatus of claim 18 wherein the capsule comprises gelatin.

22. The apparatus of claim 18 wherein the capsule dissolves after a predetermined time.

23. The apparatus of claim 18 wherein the outer sidewall of capsule comprises at least one peripheral ridge that acts as an anchoring barb prior to dissolving.

24. The apparatus of claim 23 wherein the outer sidewall capsule comprises a plurality of peripheral ridges axially spaced apart.

* * * * *